United States Patent
Dittrich et al.

(10) Patent No.: US 6,299,220 B1
(45) Date of Patent: Oct. 9, 2001

(54) COUPLING FOR SEALINGLY CONNECTING TWO ELONGATE MEDICAL INSTRUMENTS

(75) Inventors: Horst Dittrich, Immendingen; Uwe Bacher, Tuttlingen, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/155,870

(22) PCT Filed: Feb. 6, 1998

(86) PCT No.: PCT/EP98/00668

§ 371 Date: Aug. 9, 1999

§ 102(e) Date: Aug. 9, 1999

(87) PCT Pub. No.: WO98/34531

PCT Pub. Date: Aug. 13, 1998

(30) Foreign Application Priority Data

Feb. 7, 1997 (DE) .............................. 197 04 579

(51) Int. Cl.⁷ ..................................... F16L 39/00
(52) U.S. Cl. ......................... 285/317; 285/332.1
(58) Field of Search ................... 285/317, 914, 285/332, 332.1, 330

(56) References Cited

U.S. PATENT DOCUMENTS 3,948,547 * 4/1976 Gache .
4,619,640 * 10/1986 Potolsky et al. .
5,447,343 * 9/1995 Gajewski et al. ................. 285/317
5,845,943 * 12/1998 Ramacier et al. ................. 285/317

* cited by examiner

Primary Examiner—Teri Pham Luu
(74) Attorney, Agent, or Firm—St. Onge Steward Johnston & Reems LLC

(57) ABSTRACT

A coupling serves for leakproof connection of two shaft-like medical instruments (10, 90) along their shaft axis (53, 97), in particular for connection of an arthroscope shaft to an optical system. A coupling element (80) is provided, arranged on a first instrument (10) and having a contact surface (66), against whose contact surface (66) a contact surface (106) of a coupling element (92) of the second instrument (90) can be applied. Also provided is an interlock system for releasable interlocking of the two coupling elements (80, 92), the contact surfaces (64, 106) resting against one another in leakproof fashion. For easier handling, it is proposed that the interlock system have a slider (44) which is displaceable transversely to the coupling axis (53), is arranged in transversely displaceable fashion on one of the two coupling elements (80), and in a first slide position allows the two coupling elements (80, 92) to be applied against one another and in a second locking slide position mechanically interlocks the two coupling elements (80, 92). A component (58) having the contact surface (66) of at least one coupling element (80) is displaceable in the direction of the coupling axis (53).

21 Claims, 3 Drawing Sheets

COUPLING FOR SEALINGLY CONNECTING TWO ELONGATE MEDICAL INSTRUMENTS

The invention relates to a coupling for leakproof connection of two shaft-like medical instruments along their shaft axis, with a coupling element, arranged on a first instrument and having a contact surface, against whose contact surface a contact surface of a coupling element of the second instrument can be applied along a coupling axis; and with an interlock system for releasable interlocking of the two coupling elements to one another, the contact surfaces resting against one another in leakproof fashion.

A coupling of this kind is known, for example, from the applicant's company brochure "STORZ, DIE WELT DER ENDOSKOPIE" [Storz, the world of endoscopy], Arthroscopy 4th edition, 1/90. This coupling is used to connect an arthroscope shaft to an optical system.

Especially in the now-widespread technique of minimally invasive surgery, numerous procedures take place during an examination or an operation in which two medical instruments must be connected to one another and also detached again.

With this operative technique, multiple hollow shafts are introduced into the body through trocars, and then medical instruments which also have shaft-like bodies are introduced through the interior of the hollow shaft into the body.

In many procedures, it is necessary to connect the two medical instruments to one another, for which purpose the coupling cited above is required. Since body fluids or body gases can emerge through a hollow shaft introduced into the human body, it is necessary, in the case of further instruments coupled to such a shaft, for that connection to be accomplished in leakproof fashion.

The company brochure cited above shows, for example on the page labeled "ART-LJ 3", an arthroscope shaft into which an optical system shown on page "ART-LJ 2" is inserted and is intended to be connected to the arthroscope shaft.

A combination of this kind made up of the two medical instruments coupled to one another, namely arthroscope shaft and optical system, is described in the aforesaid company brochure on the introductory page of the chapter entitled "Christensen-type arthroscopic drainage system" or on the page labeled "ART-OP-INST 19" and following.

It is evident from this description of the operative technique for an arthroscopic cruciate ligament operation that frequent exchanges of the instruments connected to one another, namely arthroscope shaft and optical system, are necessary.

The coupling known from this brochure has an interlock system which is based on the bayonet principle.

One of the instruments, for example the arthroscope shaft, has a sleeve with a bayonet guide cut into its wall, into which one—or, in the case of a double bayonet guide, two—corresponding configured diametrically opposite lugs of a coupling element of the optical system must be introduced. By relative rotation of the two instruments being coupled to one another, mechanical interlocking is attained in terms of pulling along the coupling axis, which extends in the longitudinal axis of the shafts of the instruments. Because of the pitch of the bayonet thread, the instruments are moved slightly toward one another along the coupling axis, so that the corresponding contact surfaces are pressed in leakproof fashion against one another.

This coupling principle presents several disadvantages.

A first disadvantage consists in the fact that close attention is necessary when fitting the two instruments together, since the lugs of the one coupling element can be inserted into the bayonet guide of the other instrument only in a very specific rotational position.

A further disadvantage consists in the fact that during the connecting operation, the two shaft-like instruments are rotated relative to one another, for which purpose each of the two instruments must be grasped by a different hand. It should be noted that in most cases one of the two instruments has already been introduced into a human body, so that a rotation only of the other instrument to be coupled onto that instrument entails th e risk that the instrument already present in the body will also rotate, which can cause damage or injury to the patient.

Referring t o the assembly shown in the aforesaid company brochure on the page labeled "ART-OP-INST 19", it is evident that a plurality of lines, in some cases meters long and leading to monitors or other equipment, project out laterally from the optical system coupled onto the arthroscope shaft. As previously mentioned, as a result of the design of a bayonet fastener, a very specific relative position between the two instruments is defined before and after the coupling procedure has been carried out. This position may, however, be unfavorable for the surgeon, for example, and restrict his or her freedom of movement. Unfavorably projecting components can exert a torque on the assembly which is undesired, and means that the assembly must be held by the operator in strained fashion in a specific rotational position.

It is therefore the object of the present invention to develop further a coupling of the kind cited initially so that the coupling procedure can be performed without close attention and in particular with only one hand, and moreover so that the risk of harm to the patient is considerably diminished by way of improved handling and functional reliability.

According to the present invention, the object is achieved in that the interlock system has a slider which is displaceable transversely to the coupling axis, is arranged in transversely displaceable fashion on one of the two coupling elements, and in a first slide position allows the two coupling elements to be applied against one another and in a second locking slide position mechanically interlocks the two coupling elements; and that a component having the contact surface of at least one coupling element is displaceable in the direction of the coupling axis.

The first combination of features relating to the embodiment of the slider creates the possibility that the second instrument to be coupled onto the one medical instrument can be applied with the slider in the first, non-interlocking slide position, and by displacement of the slider transversely to the longitudinal axis or coupling axis, the two coupling elements of the two instruments can be mechanically interlocked with one another. The two elements need simply to be fitted onto one another, which can easily be done, for example, by feeling with one hand. The same hand can then be used to move the transversely displaceable slider without needing, for that purpose, to rotate the fitted-together parts relative to one another. This procedure can thus be performed easily and without close attention, and moreover with only one hand.

Because of the fact that at least one component of one coupling element is displaceable in the direction of the coupling axis, the contact pressure between the contact surfaces necessary for creating a leakproof closure can be created by displacing the fitted-together instruments along the coupling axis. The displacement can be caused, for example, by the transversely displaceable slider.

In a further embodiment of the invention, the component having the contact surface of at least one coupling element is displaceable, against a force, in the direction of the coupling axis toward the coupling end of that coupling element. Because this element is displaceable against a force, this force creates the contact pressure between the contact surfaces necessary to create a leakproof closure.

Achievement of the sealing closure is thus, in contrast to the situation with a bayonet interlock, no longer dependent on how far the bayonet interlock is rotated; instead the sealing pressure can be preset by the manufacturer to have a very specific force, i.e. irrespective of the practices or experience of the user, which represents a considerable advantage in terms of the functional reliability of the instruments that are coupled together.

In a further embodiment of the invention, the transversely displaceable slider is acted upon by spring force in the direction of the interlocking slide position.

This feature has the advantage that handling and operating reliability are even further simplified and enhanced by the fact that the transversely displaceable slider is acted upon by spring force in the direction of the interlocking slide position, i.e. tends to move in that direction by itself. The interlock thus cannot be released, for example due to shock or inadvertent touching of the slider. All that is needed to bring about the coupling is to displace the slider transversely against the force of the spring, which can easily be done, for example, with one finger of one hand, so that the two coupling elements can be fitted together; the slider then moves by itself into the interlocking position because of the spring force.

In a further embodiment of the invention, the transversely displaceable slider can be retained in at least one end position.

The advantage of this feature is that the slider is retained in the two defined end positions, so that when it is handled, for example set aside after first being used, it remains in that specific position and is not displaced.

For example, if an optical system were coupled to an arthroscope shaft and if the coupling were undone by displacing the transversely displaceable slider into its open, releasing position, the slider remains in that position even after the optical system has been temporarily set aside so that a different instrument can in the meantime be guided through the arthroscope shaft. When the optical system is then, after the completion of that procedure, once again placed on the arthroscope shaft, it is certain that the slider will still be in its open position. This occurs irrespective of whether the slider is arranged on the arthroscope shaft or on the optical system.

This makes a considerable contribution to simplifying the handling and operating reliability of the coupling.

In a further embodiment of the invention, retention is accomplished in the open position of the slider, and the retention is releasable by applying the other coupling element.

This feature considerably increases the simplicity with which the coupling can be handled, since on the one hand the slider, as mentioned previously, is retained in this end position and this retention is released by applying the other coupling element. Additionally combining this design with the previously mentioned feature of the slider acted upon by spring force makes this procedure particularly easy to perform. All that is necessary is to apply the other coupling element; retention of the slider is thereby released, and because of the spring force the slider is automatically displaced into the locking position.

When the connection is undone, the slider then simply needs to be displaced against the force of the spring back out from the locking position into the open position, until it is retained again in the end position; this procedure can be performed without close attention, for example with a finger, a thumb, or the like, and the connection can then be undone.

With this combination, the coupling is particularly easy to handle.

In a further embodiment of the invention, the component of the coupling element that is displaceable in the direction of the coupling axis is part of the retention system.

The advantage of this feature is that this component assumes several functions, thus resulting in a simple design which increases operating reliability. The purpose of the component that is acted upon by force and is movable in the direction of the coupling axis or longitudinal axis of the shafts is to ensure the necessary sealing pressure between the contact surfaces of the instruments to be coupled to one another. This displacement movement can now be utilized to control the retention of the slider. Thus when a coupling element of the instrument being coupled is applied to that component and the latter interlocks the slider, displacement of that component releases the interlock and the slider can be moved, or optionally in the embodiment with the slider acted upon by spring force can be moved automatically, into the interlocking position.

In a further embodiment of the invention, the slider arranged on the one coupling element has a keyhole-shaped opening through whose one larger opening region the other coupling element can be passed in the first, open slide position, and in the second, locking slide position the coupling elements are inhibited from being pulled apart in the coupling direction.

Because of its geometry, the provision of a keyhole-shaped opening of this kind makes it easier for the operator to apply the element being coupled, the reason being that the latter simply needs to be pass through the larger opening of the keyhole-shaped opening.

In a further embodiment of the invention, an undercut into which locking regions of the slider can engage in the locking slide position is provided on the other coupling element.

In combination with the keyhole-shaped slider this undercut feature, which is known per se, is reliable and particularly simple in terms of design.

In a further embodiment of the invention, radial tabs, behind which the locking regions of the slider engage into the undercut, project from the other coupling element.

This feature, also known per se, yields the advantage that coupling elements already available and known per se can be connected to the coupling element having the transversely displaceable slider that is now being proposed.

In a further embodiment of the invention, the larger opening region of the keyhole-shaped opening transitions into a smaller opening region whose lateral constrictions constitute the locking regions of the slider.

These features not only result in sliders which are easy to produce in terms of manufacturing engineering, but also constitute elements without recesses, which are thus easy to clean and sterilize.

In a further embodiment of the invention, the contact surfaces of the coupling elements are configured as conical surfaces.

This feature, known per se, has the considerable advantage that the two coupling elements rest against one another over relatively large surfaces which center themselves, so that even small contact pressures are sufficient to create a leakproof connection between the contact surfaces.

In a further embodiment of the invention, the slider is part of a transversely displaceable housing.

The advantage of this feature is that the housing surrounds the "inner" coupling element in protective fashion, the housing being a constituent which can be felt and moved, without close attention, using one finger of one hand.

In a further embodiment of the invention, a guiding surface which extends in the displacement direction of the slider, and on which a control element of the component that can be displaced in the coupling direction is guided, is provided in the housing.

The advantage of this feature is that with physically simple means, the displaceable component can be moved in defined fashion in order, for example, to bring about or undo the aforementioned interlocking of the slider.

In a further embodiment of the invention, the guiding surface has at least at one end a recess into which, when the slider is in one end position, the control element can be engaged in the coupling direction and thereby retains the slider nondisplaceably.

This also represents a feature for bringing about retention of the slider that is easy to effect mechanically.

In a further embodiment of the invention, the component that is displaceable in the coupling direction has an approximately cylindrical segment whose one end has a contact surface configured as an internal taper, and around whose exterior is arranged at least one annular elastic element which presses the component in the direction of the coupling end of the coupling element.

The conical contact surface is created using means that are physically easy to effect, and at the same time the deformable annular elastic element makes available the force necessary to create the sealing pressure in the coupling direction. A certain elasticity transverse to the coupling direction is thereby also created, however. Since this component carries the conical contact surface, this sealing cone is mounted in more or less "floating" fashion, and can accommodate minor angular changes out of the coupling axis of the contact surface of the other instrument resting against that conical surface, thus ensuring optimum sealing.

In a further embodiment of the invention, two diametrically opposite and radially projecting control pins, which rest on the guiding surface in the housing of the slider, protrude from the component.

The advantage of this feature is that by way of the control pins, the component can be guided in defined fashion along the guiding surface in the housing of the slider, and in combination with the annular elastic element that is placed around the component, a corresponding contact pressure is always present in order always to hold the control pins in contact with the guiding surface.

In a further embodiment of the invention, the component is received in a guide element which in turn is arranged in the housing of the slider.

The advantage of this feature is that the component is configured together with the guide element as a compact module, and accordingly can be preassembled and then received in protected fashion in the housing.

In a further embodiment of the invention, the guide element is connected immovably to a shaft of an instrument, and the housing of the slider is slid over the guide element; these constituents are moreover mounted on the instrument in transversely displaceable fashion via guide rods which extend through the housing and the guide element.

The guide rods serve not only to connect these two components but at the same time also to guide the housing which carries the slider, relative to the guide element that is rigidly connected to the shaft.

In a further embodiment, the guide rods are embodied as threaded studs.

The advantage of this feature is that the guide rods serve not only for guidance but also for detachable assembly of these constituents.

In a further embodiment of the invention, the guide rods are guided through a cylindrical opening in one wall of the guide element, and there is arranged in the opening a helical spring, surrounding the guide rod, which braces at one end against a shoulder of the guide rod and at the other end against an annular base of the cylindrical opening.

The considerable advantage of this feature is that the spring-assisted movement of the transversely displaceable slider is created using physically protected features of very simple design.

In a further embodiment of the invention, application of the two coupling elements against one another, with the slider in the first slide position, can be accomplished in any rotational position relative to one another.

The advantage of this feature is that application can be accomplished without particular attention, since a very specific predefined relative position between the parts to be fitted to one another is no longer necessary. With coupling elements having a circular cross section, mutual coupling can be performed in any desired rotational position.

In a further embodiment of the invention, application of the two coupling elements against one another, with the slider in the first slide position, can be accomplished only in a specific rotational position with respect to one another.

The advantage of this feature is that, if it is desired for the two medical instruments being connected to one another to be coupled to one another in a specific rotational position, this rotational position can already be attained upon application. This eliminates any subsequent alignment after the coupling is attached. A "specific rotational position" may also be understood as specific multiple rotational positions, for example rotational positions rotated 180 degrees with respect to one another, if it is possible to perform mutual coupling in those two relative positions.

It is understood that the features mentioned above and those yet to be explained below can be used not only in the respective combinations indicated, but also in other combinations or in isolation, without leaving the context of the present invention.

The invention will be described in more detail and explained below with reference to several selected exemplifying embodiments, in conjunction with the appended drawings in which.

FIGS. 1 through 5 depict, in some cases in highly schematic fashion, those components of two medical instruments 10 and 90 which are necessary in order to bring about interlocking of the two instruments 10 and 90 with one another along a shaft axis 53 or coupling axis 97.

Figure 1:
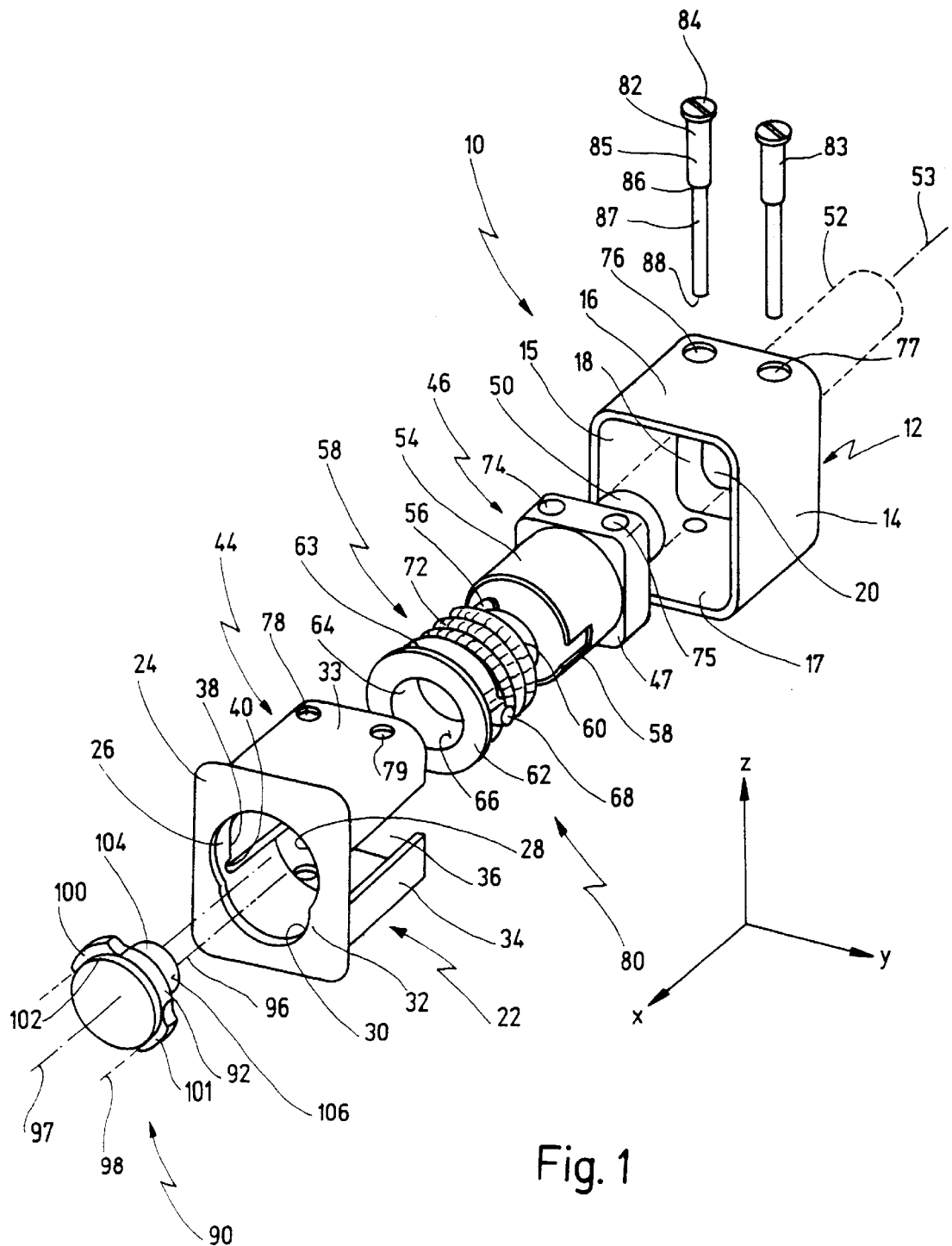
FIG. 1 shows an exploded perspective depiction of the essential components of a coupling according to the present invention.

Instrument 10 shown in FIG. 1 in an exploded depiction represents a proximal end of an arthroscope shaft whose tubular shaft 52 is sketched with dashed lines.

Instrument 10 has a cap 12 which has two rectangular sidewalls 14 and 15, extending approximately parallel and at a distance from one another, which are connected via smooth radii to an upper wall 16 and a lower wall 17.

Cap 12 is closed off by a rear wall 18 in which an oblong hole 20 is provided.

Cap 12 is open on the side facing the viewer of FIG. 1.

An intermediate housing 22, which is closed off by an end plate 24 on th e front side facing the viewer of FIG. 1, is provided. Cut out of end plate 24 is a keyhole-shaped opening 26 which has a large opening region 28 that transitions into a small opening region 30, each having an approximately circular contour. Tho se regions of end plate 24 which are arranged around small opening region 30 are referred to as the locking region 32, whose purpose will be explained later in conjunction with the manner of operation of the coupling.

Figure 3:
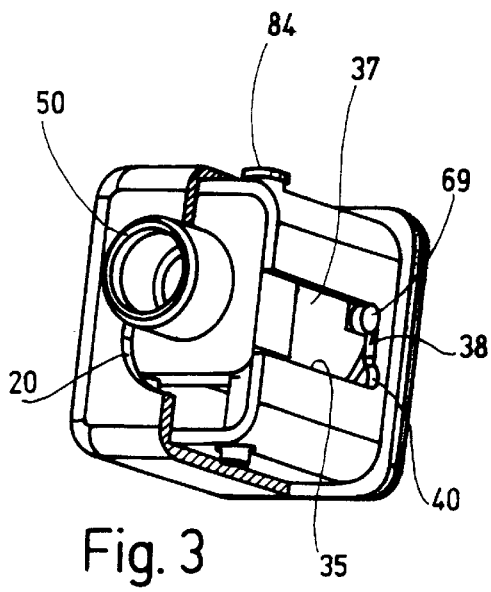
FIG. 3 shows a partially cutaway perspective depiction of the coupling according to the present invention in the operating state of FIG. 2.
Figure 5:
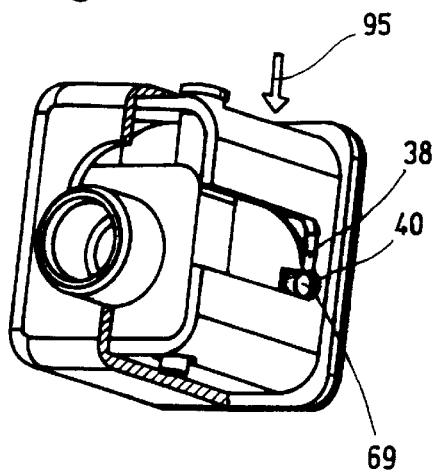
FIG. 5 shows a cutaway perspective depiction, corresponding to the depiction of FIG. 3, of the operating state of FIG. 4.

Projecting approximately at right angles from end plate 24 is a housing-like wall 33 out of each of whose opposing sidewalls 24 and 25 a respective U-shaped cutout 36 and 37 is cut (see in particular the perspective depictions of FIGS. 3 and 5).

A base of U-shaped cutouts 36 and 37 has a particularly contoured guiding surface 38 and 39 which has at one end a recess 40 and 41.

Figure 2:
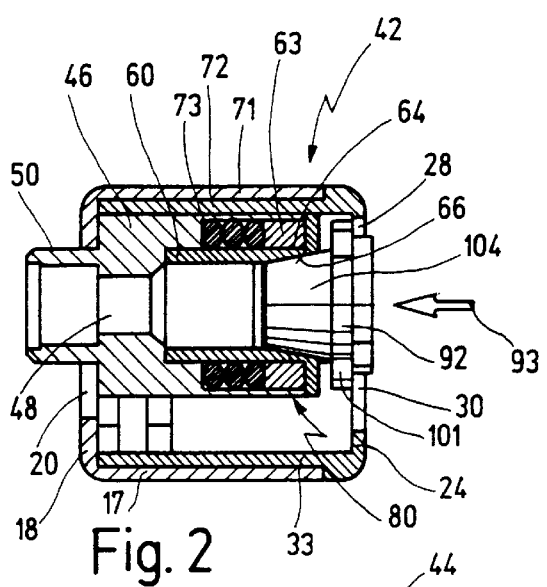
FIG. 2 shows a longitudinal section through the coupling according to the present invention, in a first operating position in which the two coupling elements have been applied against one another but not yet interlocked to one another.

Wall 33 projecting from end plate 24 is dimensioned so that its exterior can be slid into cap 12 so as to fit tightly in contact against the latter, as is evident particularly from the sectioned depiction of FIG. 2.

Once intermediate housing 22 has been slid into cap 12, what is formed overall is a housing 42 as visible in the sectioned depiction of FIG. 2, which is closed off on the side facing the viewer in FIG. 1 by end plate 24 having keyholes-shaped opening 26, and on the opposite side by rear wall 18 having oblong hole 20.

A guide element 46 arranged, in the exploded perspective depiction of FIG. 1, between cap 12 and intermediate housing 22 has a wall 47, extending perpendicular to shaft axis 53, which has in centered fashion an opening 48 (see sectioned depiction of FIG. 2). Projecting in the direction of rear wall 18 of cap 12 is a tubular flange 50 which in the assembled state (see FIG. 2) projects through elongated hole 20 in rear wall 18 of cap 12. Shaft 52 of the arthroscope, which for the sake of clarity is merely indicated by dashed lines in FIG. 1, is immovably mounted on tubular flange 50.

Projecting from the side of wall 47 located opposite tubular flange 50 is a cylindrical segment 54 which has diametrically opposite lateral U-shaped apertures 56 and 57.

Cylindrical segment 54 serves to receive a component 58.

Component 58 is configured as a tube segment 60, as is evident in particular from the sectioned depiction of FIG. 2.

Tube segment 60 has on the end facing end plate 24 a radial annular flange 62 which serves as stop for a ring 63 slid over the tube segment.

On the sides of annular flange 62, tube segment 60 has on the inner side an internal taper 64 which serves as contact surface 66 for a corresponding external taper 104 of the other instrument 90.

Projecting from ring 63 are radially and diametrically opposite control pins 68 and 69, whose radial length is such that they extend through apertures 56 and 57 in cylindrical segment 54 into cutouts 36 and 37 in intermediate housing 22.

Annular elastic elements in the form of three O-rings 71, 72, and 71 are slid over the exterior of tube segment 60 of component 58, only center O-ring 72 being shown in FIG. 1 for the sake of clarity.

Continuous orifices 74 and 75 extending transversely to the shaft axis or coupling axis 53 are provided in wall 47 of guide element 46.

In cap 12, holes 76 and 77 are provided in upper wall 16 and corresponding holes aligning therewith are provided in lower wall 17.

Also provided in the peripheral wall 33 of intermediate housing 22 are corresponding holes 78, 79 and holes on the bottom aligning with those holes.

In the assembled state, the components pulled apart along coupling axis or shaft axis 53 in the exploded depiction of FIG. 1 are slid into one another, as is evident from FIG. 2.

In this assembled state, holes 76, 77 of cap 12 align with orifices 74 and 75 of wall 47 of guide element 46, and with holes 78 and 79 of intermediate housing 22. Guide rods 82 and 83 in the form of threaded studs are passed through these aligned openings.

Each of guide rods 82 and 83 has a head 84, a first cylindrical segment 85, a shoulder 86, and a somewhat thinner cylindrical segment 87. Internal threads 88, into which a corresponding screw can be threaded from the opposite side, are provided at the lower end of the thinner cylindrical segment 87.

In the assembled state, the assemblage made up of component 58 and guide element 46 constitutes a coupling element 80. The assemblage made up of cap 12 and intermediate housing 22 constitutes a slider 44, displaceable transversely to the shaft axis or coupling axis 53, which serves as an interlock. For this purpose, the spacing between upper wall 16 and lower wall 17 of the cap is greater than the overall height of wall 47 of guide element 46.

Referring to the coordinate system shown in FIG. 1, the X axis extends in the direction of coupling axis or shaft axis 53. Guide rods 82 and 83 extend along the Z axis, i.e. slider 44 can be displaced along the Z axis relative to coupling element 80.

The purpose of coupling element 80 is to be connected to a coupling element 92 of a further instrument 90.

In the exemplary embodiment shown, instrument 90 is an optical system that is to be connected sealingly to the arthroscope shaft (instrument 10).

For this purpose, instrument 90 has a shaft 96, projecting from coupling element 92, which extends through coupling element 80 and through shaft 52 of the arthroscope up to its end closest to the patient. Opposite shaft 96 there projects from coupling element 92 a further structural segment 90 of the optical system which, for example, contains the lens system and for the sake of clarity is merely indicated here.

Coupling element 92 has radially protruding tabs 100, 101 whose radial extension is configured such that coupling element 92 can be passed through large opening region 28 of keyhole-shaped opening 26, but not through small opening region 30.

Viewed from distal to proximal, there is provided behind tabs 100, 101 an undercut 102 into which locking regions 32 of end plate 24, which delimit small opening region 30, can engage.

Tabs 100 and 101 can also be configured as a peripheral annular flange, although this is not absolutely necessary; their peripheral dimension must be selected so that in any desired rotational position of coupling element 92, a locking engagement by way of locking regions 32 of small opening region 30 of keyhole-shaped opening 26 takes place in all circumstances if coupling element 92 is aligned with smaller opening region 30.

As is evident from the sectioned depiction of FIG. 2, the three elastic O-rings 71, 72, 73 are received in an annular space so that component 58 is mounted resiliently in the direction of coupling axis or shaft axis 53, and is slightly displaceable in that direction against the return spring force of the elastic O-rings 71, 72, 73.

In the position shown in FIG. 2, slider 44 is in the open, non-locking position, i.e. internal taper 64 of component 58 aligns with large opening region 28 of keyhole-shaped opening 26. In this position, coupling element 92 of instrument 90 to be coupled with instrument 10 can then be passed through large opening region 28 of keyhole-shaped opening 26, as shown in FIG. 2 by an arrow 93. External taper 104 of coupling element 92 thereby comes into contact with internal taper 64 of component 58. The dimensions are such that tabs 100, 101 just fit through opening 26.

As is evident from FIG. 3, the radially projecting control pins 68 and 69 of component 58 rest against an upper (in the depiction of FIG. 3) end of guiding surface 38, a contact pressure being created by O-rings 71 through 73.

Figure 4:
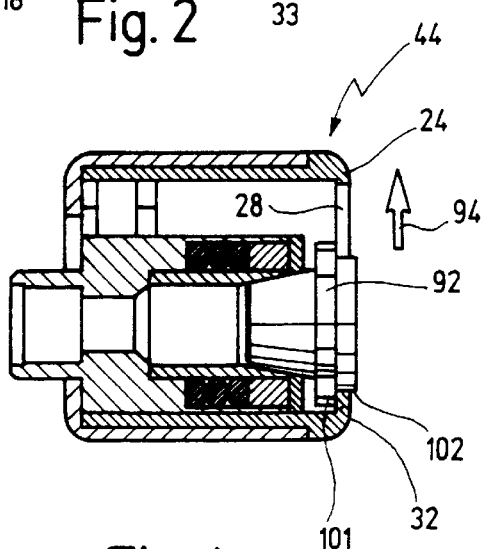
FIG. 4 shows a depiction, corresponding to FIG. 2, of the coupling according to the present invention in the interlocked state.

Internal taper 64 of component 58 is thus preloaded in the X direction. Interlocking of instruments 10 and 90 which are applied against one another via contact surfaces 96 and 106 of the two coupling elements 80 and 92 is brought about by the fact that slider 44 is displaced in the Z direction, as indicated in FIG. 4 by an arrow 94. Small opening region 30 of keyhole-shaped opening 96, or locking regions 32 of end plate 24 which surround that small opening region 30, are thereby displaced into undercut 102 behind tabs 100 and 101, and mechanically inhibit(s) any detachment of instruments 10 and 90 from one another.

During this transverse displacement of slider 44, control pins 68 and 69, as is evident from the illustration sequence from FIG. 3 to FIG. 5, have moved along guide surface 38 and have engaged into recess 40. This engagement is brought about by the pressure of the slightly compressed O-rings 71 through 73. This engagement or pressure also ensures that now, in the interlocked state, component 58 and its internal taper 64 are pressed immovably against external taper 104 of coupling element 92.

This contact pressure thus does not act until control pins 68 and 69 have engaged into recesses 40, 41, i.e. at a point in time at which coupling element 92 is already inhibited from pulling out since locking regions 32 of end plate 24 are already engaging into undercut 102. This means that during coupling, the two coupling elements 80 and 92 merely need to be applied against one another, the relative rotational position of these parts being unimportant. Slider 44 can, for example, easily be displaced with one finger of a human hand, and the additional contact pressure due to O-rings 71, 72, 73 then acts to ensure a leakproof fit for instruments 10 and 90 that are fitted and interlocked together. The "floating" mounting of component 58 in guide element 46 also, although only to a small degree, allows tilting about the Y axis without impairing the sealing fit between contact surfaces 66 and 106.

To undo the coupling, the interlock is released again by pressing on slider 44 as indicated by an arrow 95 in FIG. 5.

For this purpose, the transition from recess 40 to guiding surface 38 is configured so that gentle hand pressure on the slider disengages control pin 69 from recess 40.

Component 58 is thereby displaced somewhat in the X direction; the contact pressure on contact surfaces 96 and 106 is thereby released, and coupling element 92 can now be pulled back out of housing 42 of slider 44 through larger opening region 28.

FIGS. 6 through 11 depict a further embodiment of a coupling element 80 of an instrument 10, the essential components of which are identical to the components described in conjunction with FIGS. 1 through 5, so that these same reference characters are adopted and only the differences will be described below.

One difference consists in the configuration of guiding surface 112 in lateral cutout 35 in intermediate housing 22.

Figure 6:
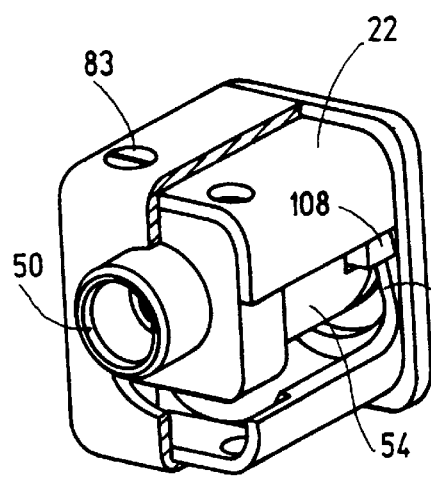
FIG. 6 shows a cutaway perspective depiction, resembling the depiction of FIG. 3, of a further embodiment of a coupling according to the present invention.
Figure 7:
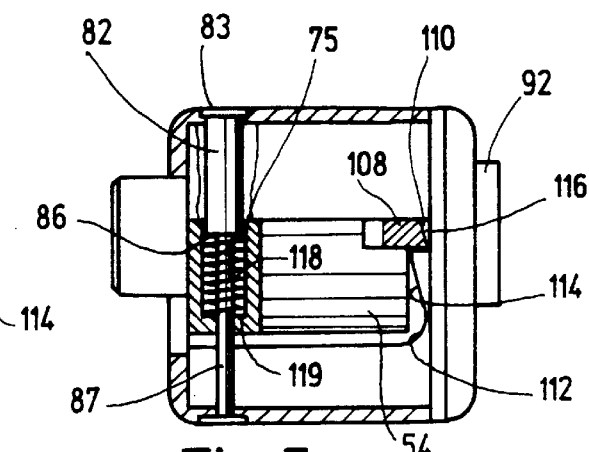
FIG. 7 shows a depiction of the coupling of FIG. 6 in longitudinal section.
Figure 8:
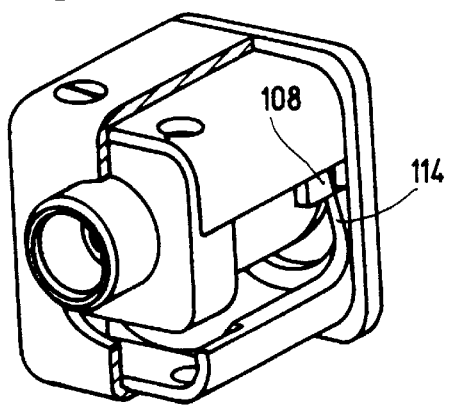
FIG. 8 shows a depiction, corresponding to FIG. 6, of the coupling in an intermediate state immediately before interlocking.

The assembled state shown in FIGS. 6 and 7 corresponds to the state described previously in conjunction with FIGS. 2 and 3, i.e. large opening region 28 of keyhole-shaped opening 26 aligns with internal taper 64 of component 58. Control pins 108 protruding from this component 58 are configured so that they have an oblique surface 110 facing the coupling point.

Guiding surface 112 has a complementary oblique surface 114, and has at its upper end (in the depiction of FIG. 7) a recess 116 into which control pin 108 can enter.

This means that control pin 108, engaged into recess 116, locks the slider in its open, non-interlocking position.

In addition, in contrast to the embodiment shown in FIGS. 1 through 5, helical springs 118 surrounding guide rods 82 and 83 are arranged in orifices 74 and 75 of wall 47 of the guide element through which guide rods 82 and 83 extend. Helical springs 118 are braced at one end against shoulder 86 of guide rods 82 and 83, and at the other end against an annular base 119 of orifices 74 and 75 that are similar to blind holes.

The thinner cylindrical segment 87 of guide rods 82 and 83 extends through annular base 119, and a corresponding screw (not shown here) is threaded into its internal threads (also not shown here). Springs 118 are preloaded in compression.

Because of the locking engagement of control pin 108 into recess 116, slider 44, in the position shown in FIGS. 6 and 7, cannot be displaced along the Z axis.

When coupling element 92 of instrument 90 is then inserted through keyhole-shaped opening 26, its external taper 104 encounters internal taper 64 of component 58. A gentle inward push, as shown in FIG. 9 by an arrow 99, causes component 58 to be displaced somewhat in the X direction against the spring force of O-rings 71 through 73.

Figure 9:
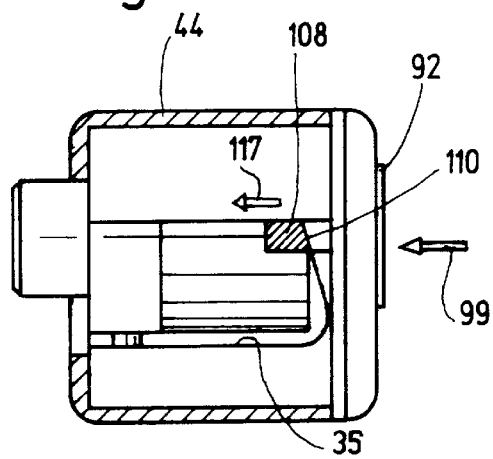
FIG. 9 shows a simplified sectioned depiction, corresponding to FIG. 7, of the position shown in FIG. 8.

Control pin 108 is thereby moved out of recess 116, as shown in FIG. 9 by an arrow 117.

Figure 10:
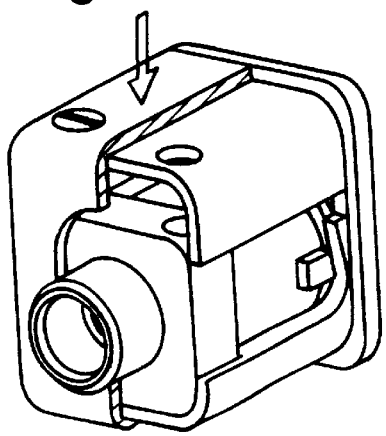
FIG. 10 shows a depiction, corresponding to FIG. 6, in the interlocked state.
Figure 11:
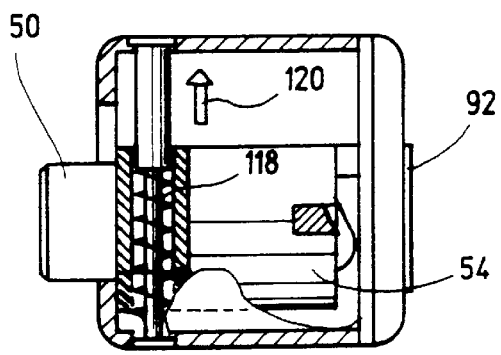
FIG. 11 shows a sectioned depiction, corresponding to FIG. 7, of the interlocked state as shown in FIG. 10.

Once control pin 108 has been disengaged out of recess 116, slider 44 can be displaced into the locking position as shown in FIGS. 10 and 11; this is accomplished automatically via the force of springs 118, as shown in FIG. 11 by an arrow 120.

Oblique surface 114 of guiding surface 112 now makes it possible, because of the pressure of O-rings 71 through 73, for component 58 again to move slightly in the X direction, so that provision is then made once again for the necessary contact pressure between contact surfaces 66 and 106.

When instrument 90 is applied against instrument 10, which again can be done in any desired angular position, a certain contact pressure merely needs to be exerted; this can be done, for example, by grasping one of the instruments between the index and middle fingers, and pushing the other toward it with the thumb of the same hand. Once control pin 108 has disengaged out of recess 116, slider 44 snaps by itself, because of the force of springs 118, into the locking position, and remains there.

To undo the coupling, slider 44 must then be pushed against the force of springs 118 in the Z direction; the fact that oblique surface 110 of control pin 108 and oblique surface 114 of guiding surface 112 slope in the same direction causes component 58 to be displaced slightly in the X direction against the pressure of O-rings 71 through 73, until control pin 108 comes to rest in front of the opening of recess 160 and then, because of the spring force of O-rings 71 through 73, snaps into it and thus mechanically inhibits slider 44 from returning.

What is claimed is:

1. A coupling for a leakproof connection of two medical instruments, each medical instrument having a shaft, said coupling is performed along a coupling axis extending along a shaft axis of said shafts of said medical instruments, having
   a first coupling element arranged on a first medical instrument, said first coupling element having a first contact surface,
   a second coupling element arranged on a second medical instrument, said second coupling element having a second contact surface, said first contact surface of said first coupling element can be brought into contact with said second contact surface of said second coupling element along said coupling axis, and
   an interlock system for releasable interlocking the two coupling elements to one another, with said contact surfaces resting against one another in a leakproof fashion, wherein
   said interlock system has a slider which is displaceable transversely to said coupling axis between a first position and a second position, and said slider is arranged in transversely displaceable fashion at one of said two coupling elements;
   said slider allowing in said first position the two coupling elements to be applied against one another, and in said second position mechanically interlocking the two coupling elements,
   wherein at least one of said coupling elements is provided with a component having said contact surface of said coupling element, said component being displaceable in direction of said coupling axis, and
   wherein said contact surfaces of said coupling elements are configured as conical surfaces.

2. The coupling of claim 1, wherein said component is displaceable against a force and in a direction opposite to a coupling and of said coupling element provided with said component.

3. The coupling of claim 1, wherein said transversely displaceable slider is acted upon by a spring force in a direction directed to the second interlocking position of said slider.

4. The coupling of claim 1, wherein said transversely displaceable slider can be retained in at least one of its positions.

5. The coupling of claim 4, wherein said transversely displaceable slider is retained in its first open position, and said slider is released by applying the other coupling element to said coupling element having arranged said slider.

6. The coupling of claim 5, wherein said component that is displaceable in the direction of the coupling axis is part of a retention system retaining said displaceable slider.

7. The coupling of claim 1, wherein said slider is part of a transversely displaceable housing.

8. The coupling of claim 7, wherein a guiding surface is provided in said housing, said guiding surface extends in direction of displacement of said slider, a control element provided on said component that can be displaced in said coupling direction is guided by said guiding surface.

9. The coupling of claim 8, wherein said guiding surface has a recess on at least one end thereof, into which recess said control element can be engaged in the direction of performing said coupling, thereby said slider is in one of its positions, and said control element retains said slider non-displaceably transversely to said direction of performing said coupling.

10. The coupling of claim 1, wherein said component that is displaceable in said coupling direction has an approximately cylindrical segment whose one end has a contact surface configured as an internal taper, and around whose exterior at least one annular elastic element is arranged, which at least one annular elastic element presses said component in a direction of a coupling end of said coupling element.

11. The coupling of claim 10, wherein at least two diametrically opposite and radially projecting control pins are provided on said component, which control pins rest on a guiding surface of a housing of said slider.

12. The coupling of claim 11, wherein said component is received in a guide element which in turn is arranged in said housing of said slider.

13. The coupling of claim 12, wherein said guide element is connected immovably to a shaft of one of said medical instruments, said housing of said slider is slid over said guide element, and these constituents are mounted on said medical instrument in transversely displaceable fashion via guide rods which extend through said housing in said guide element.

14. The coupling of claim 13, wherein said guide rods are embodied as threaded studs.

15. The coupling of claim 14, wherein said guide rods are guided through a cylindrical opening in one wall of said guide element, and helical springs are arranged in said cylindrical openings surrounding said guide rods, each helical spring braces at one end against a shoulder of a guide rod and at the other end against an annular base of said cylindrical opening.

16. The coupling of claim 1, wherein an application of the two coupling elements against one another, with said slider in said first open position, can be accomplished in any rotational position relative to one another.

17. The coupling of claim 1, wherein an application of the two coupling elements against one another, with said slider in said first open position, can be accomplished only in a specific rotational position with respect to one another.

18. A coupling for a leakproof connection of two medical instruments, each medical instrument having a shaft, said coupling is performed along a coupling axis extending along a shaft axis of said shafts of said medical instruments, having a first coupling element arranged on a first medical instrument, said first coupling element having a first contact surface, a second coupling element arranged on a second medical instrument, said second coupling element having a second contact surface, said first contact surface of said first coupling element can be brought into contact with said second contact surface of said second coupling element along said coupling axis, and an interlock system for releasable interlocking the two coupling elements to one another, with said contact surfaces resting against one another in a leakproof fashion, wherein said interlock system has a slider which is displaceable transversely to said coupling axis between a first position and a second position, and said slider is arranged in transversely displaceable fashion at one of said two coupling elements;

said slider allowing in said first position the two coupling elements to be applied against one another, and in said second position mechanically interlocking the two coupling elements, wherein at least one of said coupling elements is provided with a component having said contact surface of said coupling element, said component being displaceable in direction of said coupling axis, wherein said slider arranged on one of the two coupling elements has a keyhole-shaped opening having a larger opening region, through said larger opening region the other coupling element can be passed in the first, open slide position of said slider, and in the second, locking position of said slider, said two coupling elements are locked from being pulled apart in direction of the coupling axis, and wherein said contact surfaces of said coupling elements are configured as conical surfaces.

19. The coupling of claim 18, wherein said other coupling element to be passed through said keyhole-shaped opening is provided with an undercut, into which undercut locking regions of said slider can be engaged in said second locking position of said slider.

20. The coupling of claim 19, wherein radial tabs project from said other coupling element behind which tabs said locking regions of said slider engage into the undercut.

21. The coupling element of claim 20, wherein said larger opening region of said keyhole-shaped opening transitions into a smaller opening region, whose lateral constrictions constitute said locking regions of said slider.

* * * * *